United States Patent
Hong (10) Patent No.: US 9,510,975 B2
(45) Date of Patent: Dec. 6, 2016

(54) EYE PROTECTION DEVICE (71) Applicant: TZOO YING ENTERPRISE CO., LTD., Kaohsiung (TW)

(72) Inventor: Rong-Tai Hong, Kaohsiung (TW)

(73) Assignee: TZOO YING ENTERPRISE CO., LTD, Kaohsiung (TW)

( * ) Notice: Subject to any disclaimer, the term of this patent is extended or adjusted under 35 U.S.C. 154(b) by 222 days.

(21) Appl. No.: 14/217,315

(22) Filed: Mar. 17, 2014

(65) Prior Publication Data

US 2014/0338109 A1    Nov. 20, 2014

(30) Foreign Application Priority Data

May 16, 2013  (TW) .............................. 102117350 A (51) Int. Cl.
*A61F 9/02* (2006.01)
*A61F 9/04* (2006.01)

(52) U.S. Cl.
CPC .............. *A61F 9/02* (2013.01); *A61F 9/045* (2013.01); *A61F 9/022* (2013.01)

(58) Field of Classification Search
CPC ............ A61F 9/04; A61F 9/022; A61F 9/024; A61F 13/124; A61F 13/00029; A61F 2013/00165; A61F 9/045; A61F 9/02; A61F 9/025; A61F 9/029; A61F 2013/00251; G02C 7/16; G02C 7/165
USPC ... 2/15, 11, 440, 442, 445; 128/858; 351/45, 351/46; 602/47, 41–43, 74
See application file for complete search history.

(56) References Cited

U.S. PATENT DOCUMENTS

| | | | | |
|---|---|---|---|---|
| 459,563 A | * | 9/1891 | Groh | G02C 7/16 351/46 |
| 709,058 A | * | 9/1902 | Stierle | A61H 5/00 351/202 |
| 839,016 A | * | 12/1906 | MacDonald | G02B 5/1842 351/46 |
| 1,247,853 A | * | 11/1917 | McWenie | G02C 7/16 2/433 |
| 1,270,640 A | * | 6/1918 | Markham | G02C 7/16 2/15 |
| 1,313,262 A | * | 8/1919 | Compere | A61B 3/135 351/214 |
| 1,743,510 A | * | 1/1930 | Zickmantel | G02C 7/16 2/15 |
| 1,844,232 A | * | 2/1932 | Tharp | G02C 7/16 2/13 |
| 1,876,769 A | * | 9/1932 | Sheffield | G02C 7/16 351/46 |
| 2,642,569 A | * | 6/1953 | Triebes | G02C 7/16 2/433 |
| 3,333,586 A | * | 8/1967 | Bellis | A61F 9/022 2/12 |

(Continued)

*Primary Examiner* — Amy Vanatta (57) ABSTRACT

An eye protection device a first covering sheet, a protection sheet, and a second covering sheet. The first covering sheet has a first supporting edge with a containment slot and a first opening disposed on the first supporting edge. The protection sheet is disposed in the containment slot and has a non-transparent sheet and an axial aperture provided in the sheet. The second covering sheet has a second supporting edge and a second opening provided on the second supporting edge. The second supporting edge overlaps the first supporting edge, and the first and second supporting edges sandwich the protection sheet in the containment slot.

10 Claims, 7 Drawing Sheets

(56) References Cited

U.S. PATENT DOCUMENTS

| | | | | | |
|---|---|---|---|---|---|
| 3,416,522 | A | * | 12/1968 | Yeremian | A61F 13/00029 |
| | | | | | 128/889 |
| 4,862,902 | A | * | 9/1989 | Goffman | A61F 9/04 |
| | | | | | 128/858 |
| 4,867,146 | A | * | 9/1989 | Krupnick | A61F 9/00 |
| | | | | | 128/858 |
| 4,890,608 | A | * | 1/1990 | Steer | A61F 5/443 |
| | | | | | 602/52 |
| 6,092,243 | A | * | 7/2000 | Wu | A61F 9/025 |
| | | | | | 2/426 |
| 6,131,208 | A | * | 10/2000 | Banks | A61F 9/04 |
| | | | | | 128/858 |
| 6,320,094 | B1 | * | 11/2001 | Arnold | A61F 13/124 |
| | | | | | 128/858 |
| 6,592,221 | B1 | * | 7/2003 | Stregova | G02C 7/165 |
| | | | | | 351/203 |
| 7,584,754 | B1 | * | 9/2009 | Pellegrini | A61F 9/04 |
| | | | | | 128/858 |
| 7,748,387 | B1 | * | 7/2010 | Vu | A61F 9/04 |
| | | | | | 128/858 |
| 2011/0004969 | A1 | * | 1/2011 | Frohlich | A61F 9/04 |
| | | | | | 2/15 |

* cited by examiner

EYE PROTECTION DEVICE

BACKGROUND OF THE INVENTION

1. Field of the Invention

The present invention relates to an eye protection device, and more particularly to an eye protection device having a non-transparent and anti-electromagnetic wave.

2. Description of the Related Art

With technology improvement, people often have multiple portable electronic devices such as smartphone, panel computer . . . etc., therefor, they tend to over use their eyes too much and have fatigue eye condition. In addition, fatigue eye condition can get worsen without proper treatments.

Furthermore, the portable electronic devices generates electromagnetic waves, since eye tissue contains a lot of moisture which tends to absorb electromagnetic wave, which can cause fatigue, discomfort and dryness.

Moreover, the portable electronic devices generates strong light to user's eyes which can be exhausting.

Therefore, it is desirable to provide an eye protection device to mitigate and/or obviate the aforementioned problems.

SUMMARY OF THE INVENTION

An objective of the present invention is to provide an eye protection device.

In order to achieve the above mentioned objective, the eye protection device a first covering sheet, a protection sheet, and a second covering sheet. The first covering sheet has a first supporting edge with a containment slot and a first opening disposed on the first supporting edge. The protection sheet is disposed in the containment slot and has a non-transparent sheet and an axial aperture provided in the sheet. The second covering sheet has a second supporting edge and a second opening provided on the second supporting edge. The second supporting edge overlaps the first supporting edge, and the first and second supporting edges sandwich the protection sheet in the containment slot.

Other objects, advantages, and novel features of the invention will become more apparent from the following detailed description when taken in conjunction with the accompanying drawings.

DETAILED DESCRIPTION OF THE PREFERRED EMBODIMENT

Figure 1:
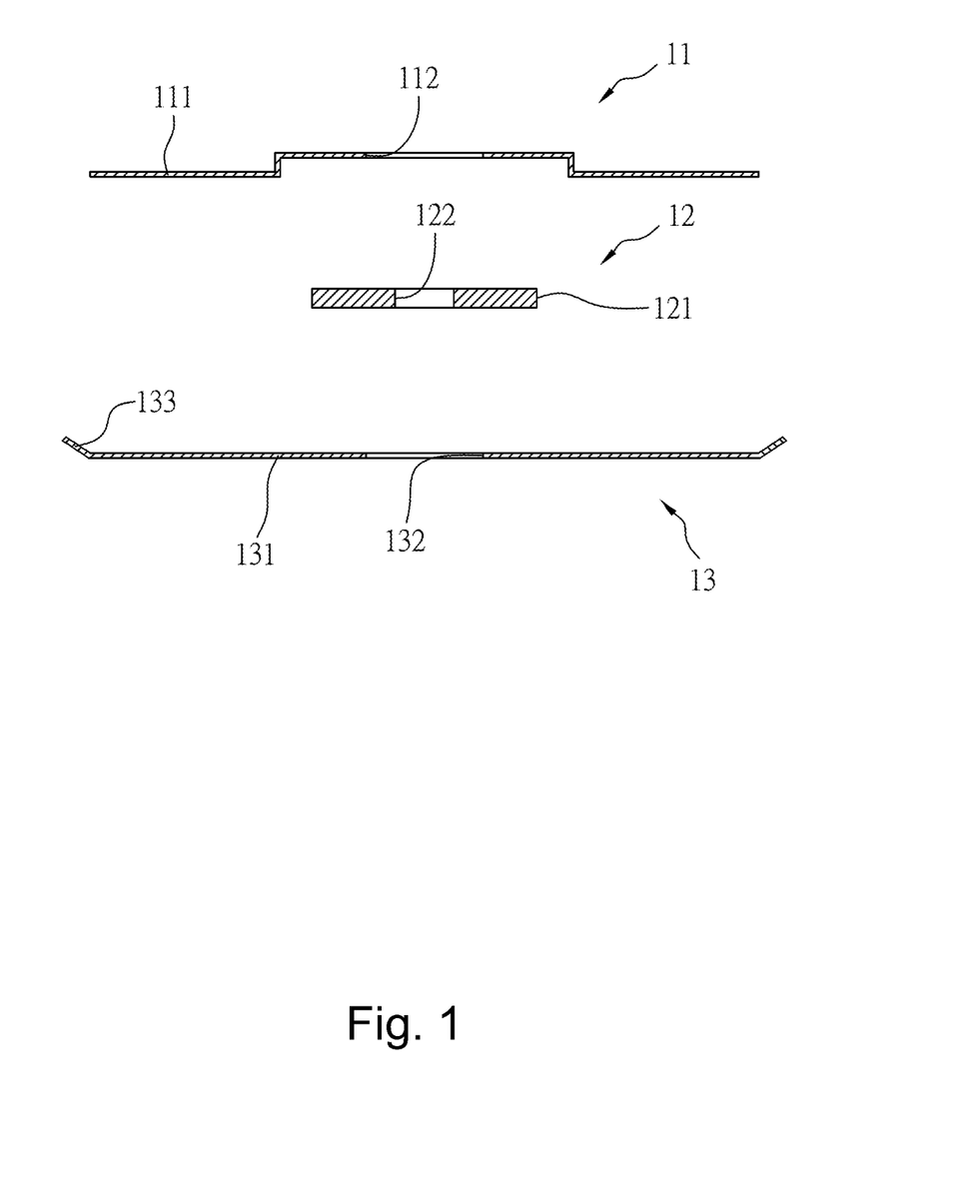
FIG. 1 is an exploded cross-sectional view of an eye protection unit according to a first embodiment of the present invention.
Figure 2:
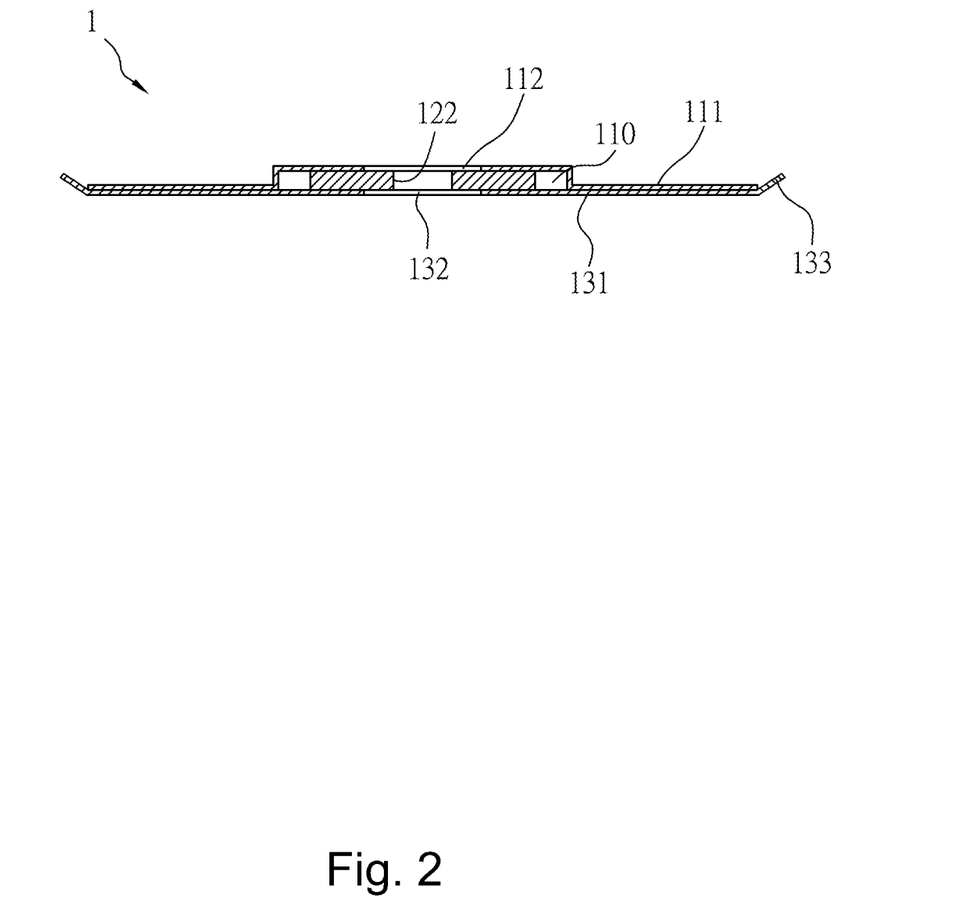
FIG. 2 is an assembled cross-sectional view of the eye protection unit according to the first embodiment of the present invention.
Figure 3:
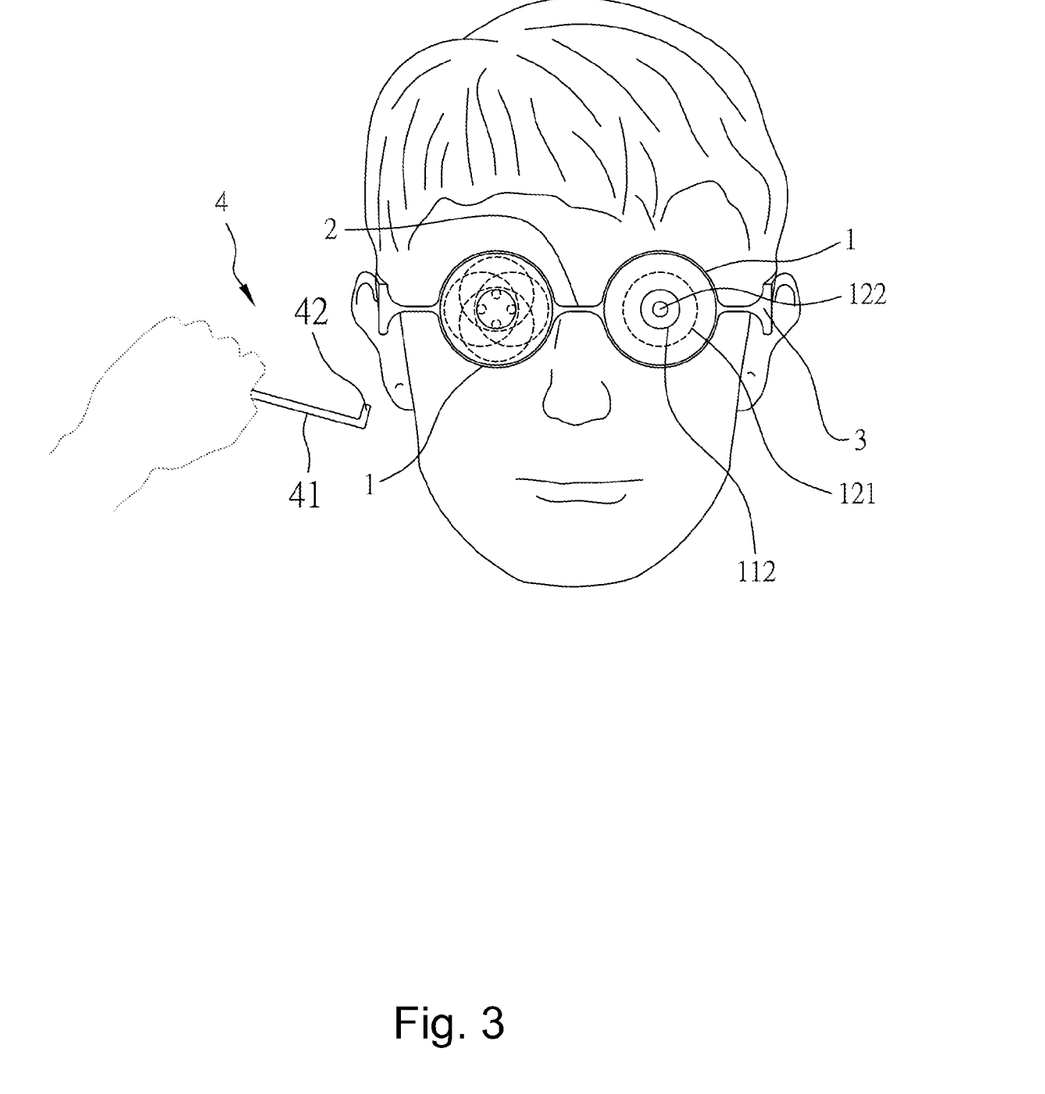
FIG. 3 is a perspective schematic drawing of the eye protection unit according to the first embodiment of the present invention.

Please refer to FIG. 1, and FIG. 2 and FIG. 3. In a first embodiment, an eye protection device comprises: two eye protection units 1, a connecting member 2 connecting the two eye protection units 1 and two supporting legs 3 respectively connected to opposite sides of the two eye protection units 2 and an adjusting member 4. The two eye protection units 1, the connecting member 2 and the two supporting legs 3 together compose an eyeglasses-like structure.

In addition, in this first embodiment of the present invention, the eye protection device includes two eye protection units 1, but if a user only needs treatment for one eye, the eye protection device can only provide one eye protection units 1.

Figure 4:
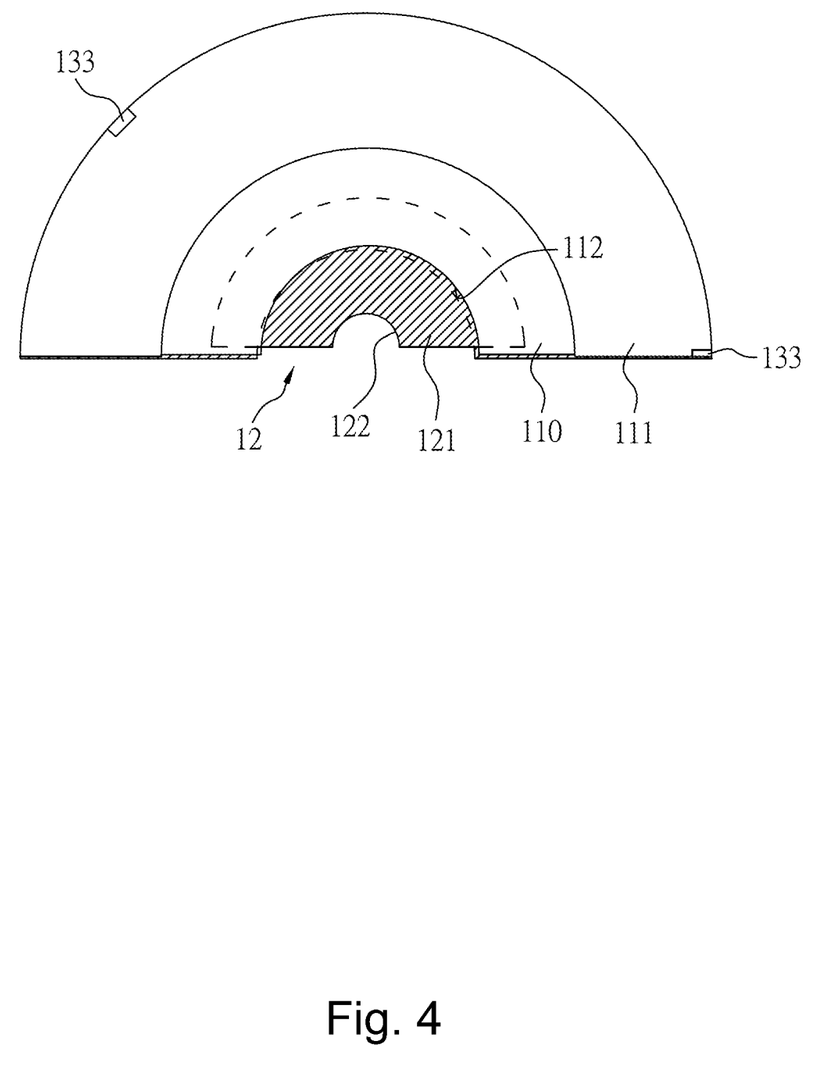
FIG. 4 is a top view of the eye protection unit according to the first embodiment of the present invention.

Please refer to FIG. 4, the two eye protection units 1 respectively comprises a first covering sheet 11, a protection sheet 12, and a second covering sheet 13. The first covering sheet 11 has a first supporting edge 111 with a containment slot 110 and a first opening 112 disposed on the first supporting edge 111.

The protection sheet 12 is approximately circular and disposed in the containment slot 110 and has a non-transparent sheet 121 and an axial aperture 122 provided in the sheet 121. The sheet 121 is made from materials selected from iron, steel, and other magnetizeable metals.

When the electromagnetic waves reaches to a metal surface, the free electrons in the metal is affected by the electrical field caused by the electromagnetic waves and start to vibrate with the same frequency as the electromagnetic waves by the energy provide from electromagnetic waves. Therefore, metal can shield the electromagnetic waves by absorbing the energy provide from electromagnetic waves.

The second covering sheet 13 has a second supporting edge 131, and a second opening 132 is provided on the second supporting edge 131. The second supporting edge 131 overlaps the first supporting edge 111, and the first and second supporting edges 111, 131 sandwich the protection sheet 121 in the containment slot 110. In addition, the protection sheet 12 is positioned in the containment slot 110, the first and second supporting edges 111, 131 limit the up and down movements of the protection sheet 12 but not the left and right movements. Therefore, a diameter of the protection sheet 12 is relatively smaller than a diameter of the containment slot 110 such that the protection sheet 12 is capable of moving in the containment slot 110.

Moreover, the second supporting edge 131 further has a plurality of folded edges 133, and the plurality of folded edges 133 are used for positioning the first supporting edge 111 so the first and second supporting edges 111, 131 are combined together.

Figure 5:
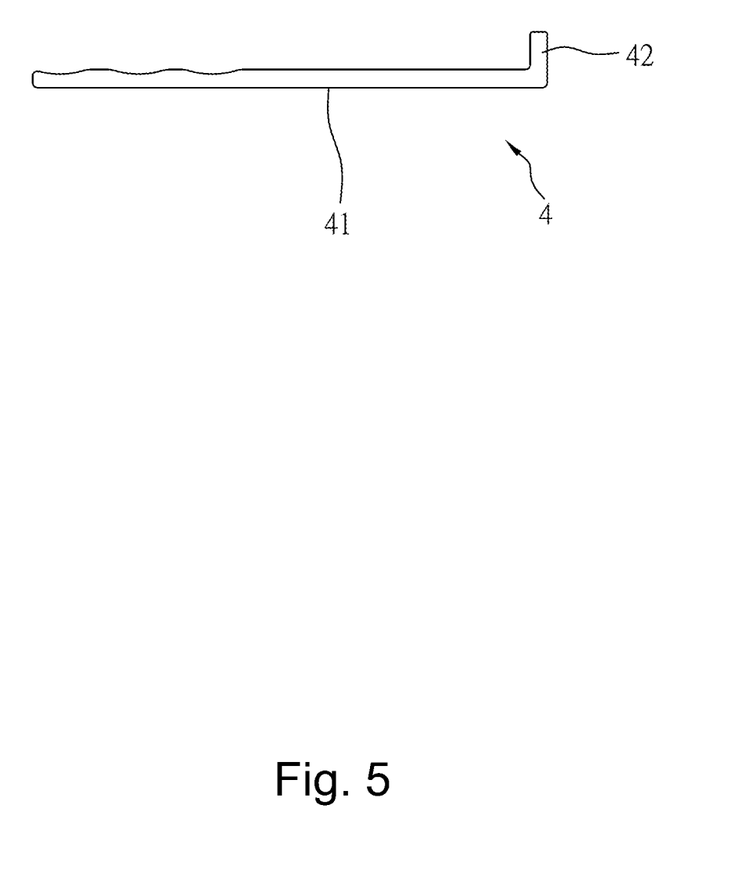
FIG. 5 is a side view of the eye protection unit according to the first embodiment of the present invention.

Please refer to FIG. 5, the adjusting member 4 comprises a holding rod 41 and extension 42 at an end of the holding rod 41. The holding rod 41 is configured for being held by the user, and the extension 42 is acceptable in the axial aperture 122 of the protection sheet 12. When the user places the extension 42 into the axial aperture 122 of the protection sheet 12 and pulls the holding rod 41 to adjust the position of the protection sheet 12 in the containment slot 110 for different eye distance and face widths.

Figure 6:
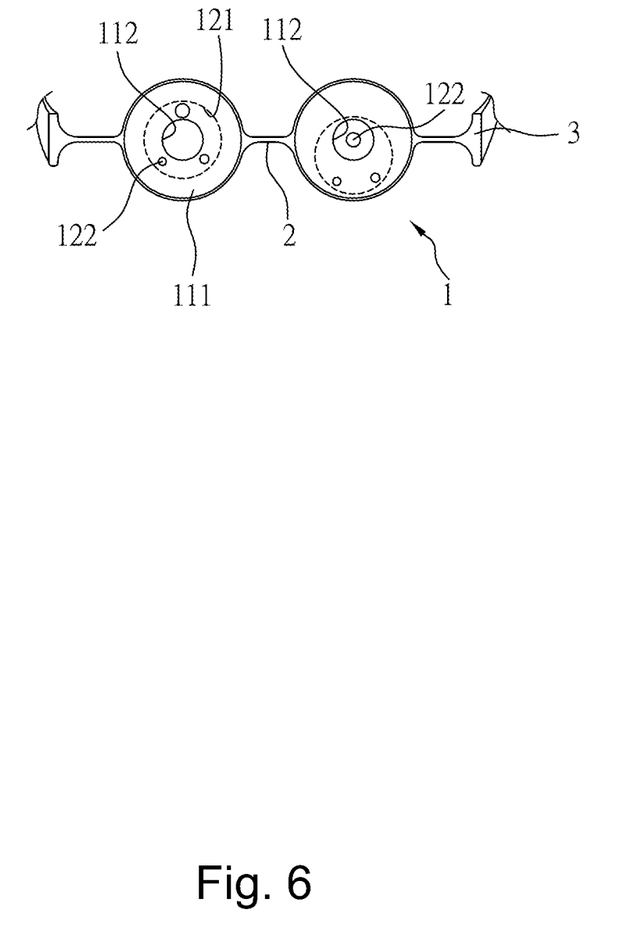
FIG. 6 is a front view of the eye protection unit according to a second embodiment of the present invention.

Please refer to FIG. 6. In a second embodiment of the present invention, a main difference than the first embodiment is: the sheet 121 has a plurality of axial apertures 122 with different diameters, and only one axial aperture 122 is uncovered by the first supporting edge 111 on the first opening 112. The plurality of axial apertures 122 with different diameters are suitable for users having different pupil sizes of the eyes.

Figure 7:
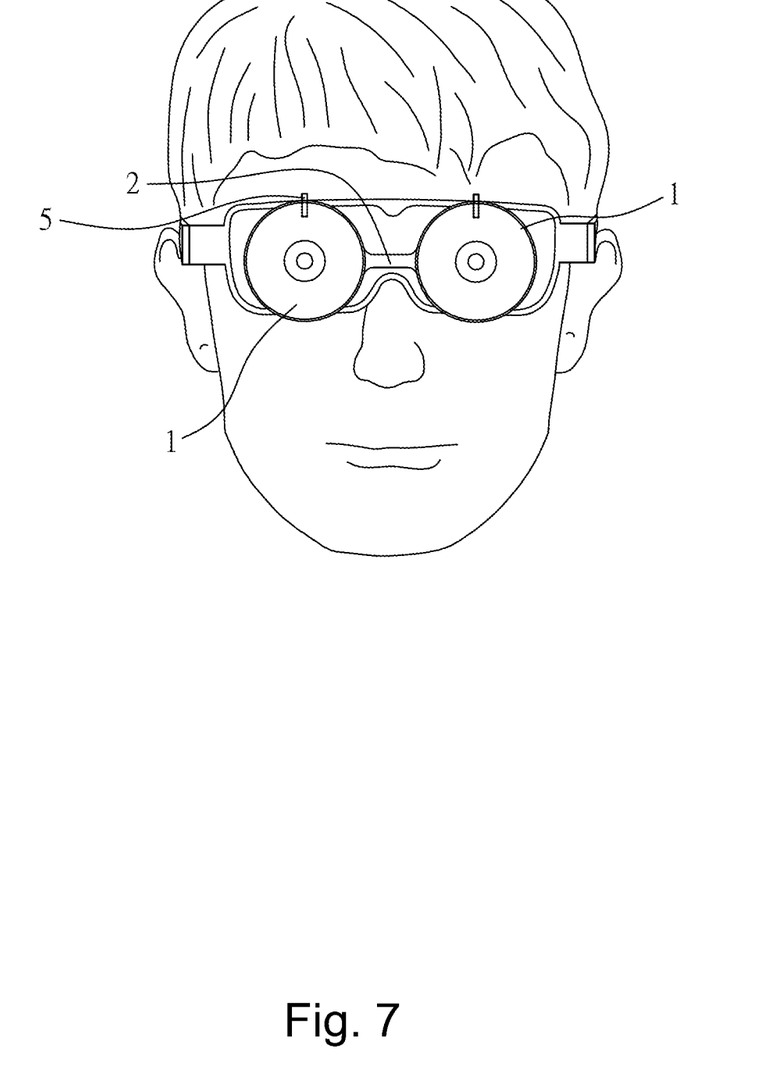
FIG. 7 is perspective schematic drawing of the eye protection unit according to a third embodiment of the present invention

Please refer to FIG. 7, in a third embodiment of the present invention, a main difference than the first embodiment is: the eye protection device comprises two eye protection units 1, a connecting member 2, and two positioning members 5.

The connecting member 2 connects the two eye protection units 1, the two positioning members 5 is respectively disposed at an upper edge of the two eye protection units 1. In the third embodiment, the positioning member 5 is a hook, which can be attached onto a pair of eye glasses.

In addition, the two positioning member 5 can also utilizes other manners to be attached onto the eye glasses such as magnetic attachment or clamping attachment.

With the above-mentioned description, following benefits can be obtained:

1. Providing Shielding Effect

Since the sheet 121 is made of magnetizeable metal which can shield off the electromagnetic waves, and the non-transparent sheet 121 can block unnecessary light for the user's eyes.

2. Adjustable View Angle

When the user holds the holding rod 41 and places the extension into the axial aperture 122 of the protection sheet 12 and pulls the holding rod 41 to adjust the position of the protection sheet 12 in the containment slot 110 for different eye distance and face widths.

3. Protecting Eyes by Limiting the Visual Range

With the axial aperture 122 of the sheet 121, the visual range of the user will be limited, which can prevent incorrect eye usage.

Consequently, the two eye protection units 1, the connecting member 2, and the supporting legs 3 compose an eyeglasses-like structure. With the first covering sheet 11, the protection sheet 12, the second covering sheet 13 and the plurality of folded edges 133, the first opening 112, the axial aperture 122 and the second opening 132 can be aligned with each other for correct visual range. the sheet 121 can shield off the electromagnetic waves, and the non-transparent sheet 121 can block unnecessary light for the user's eyes. Furthermore, when the user holds the holding rod 41 and places the extension into the axial aperture 122 of the protection sheet 12 and pulls the holding rod 41 to adjust the position of the protection sheet 12 in the containment slot 110 for different eye distance and face widths.

Although the present invention has been explained in relation to its preferred embodiment, it is to be understood that many other possible modifications and variations can be made without departing from the spirit and scope of the invention as hereinafter claimed.

What is claimed is:

1. An eye protection device comprising:
an eye protection unit comprising:
a first covering sheet having a first supporting edge with a containment slot and a first opening disposed in the first covering sheet;
a protection sheet movably disposed in the containment slot and comprising a metallic, opaque sheet with an axial aperture provided in the opaque sheet; and
a second covering sheet having a second supporting edge and a second opening provided in the second covering sheet at least partly aligned with the first opening, the second supporting edge overlapping the first supporting edge, and the first and second supporting edges sandwiching the protection sheet in the containment slot;
wherein the protection sheet is movable to adjust a position of the axial aperture with respect to the first and second openings to adjust light reaching a user's eye via the first opening, the axial aperture and the second opening.

2. The eye protection device as claimed in claim 1, further comprising another eye protection unit, a connecting member connecting the two eye protection units and two supporting legs respectively connected to opposite sides of the two eye protection units.

3. The eye protection device as claimed in claim 2 further comprising an adjusting member having a holding rod and an extension connected to an end of the holding rod.

4. The eye protection device as claimed in claim 3, wherein the second supporting edge is provided with a plurality of folded edges, and the plurality of folded edges are used for positioning the first supporting edge.

5. The eye protection device as claimed in claim 1, wherein the opaque sheet further includes a plurality of axial apertures with different diameters, and only one axial aperture is uncovered by the first opening to allow light to reach the user's eye via the one axial aperture.

6. The eye protection device as claimed in claim 1, wherein the opaque sheet is made from materials selected from iron, steel, and other magnetizeable metals.

7. The eye protection device as claimed in claim 6 further comprising: another eye protection unit and a connecting member connecting the two eye protection units and positioning members respectively connected to opposite sides of the two eye protection units.

8. The eye protection device as claimed in claim 7 further comprising an adjusting member, the adjusting member having a holding rod and an extension connected to an end of the holding rod.

9. The eye protection device as claimed in claim 1, wherein the second supporting edge is provided with a plurality of folded edges, and the plurality of folded edges are used for positioning the first supporting edge.

10. The eye protection device as claimed in claim 9, wherein the opaque sheet further has a plurality of axial apertures with different diameters, and only one axial aperture is uncovered by the first opening to allow light to reach the user's eye via the one axial aperture.

* * * * *